United States Patent
Blakley et al.

(12) 
(10) Patent No.: US 6,871,535 B2
(45) Date of Patent: Mar. 29, 2005

(54) FLOW DIRECTION DETECTOR

(75) Inventors: Daniel R. Blakley, Corvallis, OR (US); David Orr, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 83 days.

(21) Appl. No.: 10/219,424

(22) Filed: Aug. 14, 2002

(65) Prior Publication Data

US 2004/0031331 A1 Feb. 19, 2004

(51) Int. Cl.[7] .............................. G01F 1/68; G01F 1/37
(52) U.S. Cl. ................................ 73/204.22; 73/204.21; 73/861.52; 73/861.63
(58) Field of Search .................... 73/861.52, 861.63, 73/861.64, 204.21, 204.22

(56) References Cited

U.S. PATENT DOCUMENTS

| | | |
|---|---|---|
| 3,777,563 A * | 12/1973 | Yamasaki et al. ......... 73/861.22 |
| 4,776,214 A | 10/1988 | Moran et al. |
| 4,787,251 A * | 11/1988 | Kolodjski ................. 73/861.63 |
| 4,969,357 A | 11/1990 | Mickler |
| 5,035,138 A | 7/1991 | Abdel-Rahman |
| 5,108,193 A | 4/1992 | Furubayashi |
| 5,209,111 A | 5/1993 | Agarwal et al. |
| 5,237,866 A | 8/1993 | Nijdam |
| 5,415,029 A | 5/1995 | Uchiyama et al. |
| 5,511,415 A | 4/1996 | Nair et al. |
| 5,515,295 A | 5/1996 | Wang |
| 5,524,084 A | 6/1996 | Wang et al. |
| 5,780,736 A | 7/1998 | Russell |
| 5,869,758 A | 2/1999 | Huiberts |
| 5,929,333 A | 7/1999 | Nair |
| 5,952,571 A | 9/1999 | Arai et al. |
| 6,253,606 B1 * | 7/2001 | Yonezawa et al. ....... 73/204.26 |
| 6,546,812 B2 * | 4/2003 | Lewis ..................... 73/861.63 |

* cited by examiner

*Primary Examiner*—Harshad Patel

(57) ABSTRACT

A flow direction detector is provided which includes a flow disruptor positioned in a fluid flow path to effect a detectable differential flow characteristic to such flow path based on fluid flow direction, and a sensor arrangement configured to detect such detectable differential flow characteristic within the flow path.

16 Claims, 3 Drawing Sheets

FLOW DIRECTION DETECTOR

BACKGROUND ART

Various types of technology involve the precisely timed injection of a vaporized fluid into an air stream. This technology may be used in such different fields as fuel injection systems and metered dose inhalers. While used for vastly differing applications, these technologies typically would benefit from a reliable mechanism for detecting the flow direction of the air stream into which the vaporized fluid is injected.

For example, metered dose inhalers provide a much-needed drug-delivery method that allows patients to aspirate a "puff" of medication rather than swallow a pill, or drink or inject liquid medication. In some cases, as with medications that directly target the patient's lungs, aspiration enables the medicine to reach the target area more quickly. In addition, aspiration is typically considered to be less painful than other drug-delivery methods.

However, metered dose inhalers typically rely on the user inhaling at the same time as the aforementioned "puff" is expelled. If the user miss-times the moment of inhalation, for example, exhaling at the time the puff is expelled, the user may receive an incorrect dose, or no dose at all. Because the user might not know whether or not a correct dose has been administered, the patient may sometimes be forced to choose between skipping a dose and administering a second dose that could lead to possible over-dosing. Depending upon the particular medication being administered, either of these scenarios could have negative consequences. Thus, implementation of an airflow direction detection mechanism may also be useful in metered dose inhalers.

One previously-described method of airflow speed detection is hot wire anemometry. In general, hot wire anemometry relies on the cooling effect of airflow across a heated wire. Typically, hot wire anemometry uses two wires, a hot wire, which acts as the power dissipative element, and a resistance wire, which acts as a reference element, in a bridge circuit. The output voltages of the two wires in the circuit are held equal by regulating the heating current. When incoming air passes over the hot wire, the control circuit must apply more voltage to keep the hot wire at the original temperature differential. The control unit detects this increase in voltage. The greater the mass flow rate, the greater the voltage required to maintain the temperature differential. Mass flow rate thus may be determined based on the voltage required to maintain the desired temperature differential. However, while detection of mass flow rate is often useful, this method has not been capable of detecting flow direction.

SUMMARY OF THE INVENTION

A flow direction detector is provided which includes a flow disrupter positioned in a fluid flow path to effect a detectable differential flow characteristic to such flow path based on fluid flow direction, and a sensor arrangement configured to detect such detectable differential flow characteristic within the flow path.

DETAILED DESCRIPTION

Figure 1:
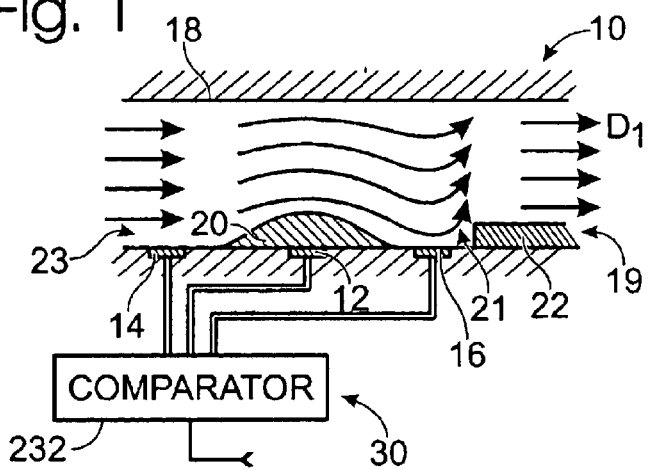
FIG. 1 is a somewhat schematic illustration of a flow direction detector according to one embodiment of the present invention, fluid being shown flowing in a first direction.
Figure 2:
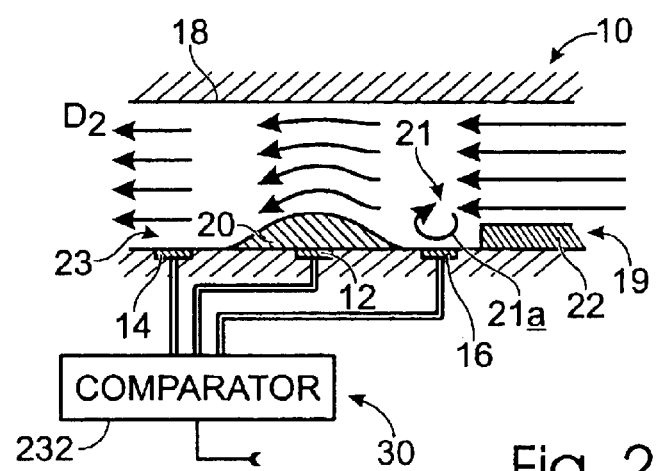
FIG. 2 is a somewhat schematic illustration of the flow direction detector of FIG. 1, but showing fluid flow in a second direction opposite the first direction.

The present invention provides a flow direction detector, an exemplary form of which is indicated generally at 10 in FIGS. 1 and 2. As shown, flow direction detector 10 may include a plurality of temperature sensors 12, 14 and 16 located along a flow path defined by a tube 18. The temperature sensors, it will be appreciated, may be adapted to detect the temperature of a fluid stream at different points along the flow path. One or more of the temperature sensors may serve as a reference, the remaining temperature sensors being exposed to the fluid flowing within tube 18 for use in determining flow presence, flow direction, and/or flow rate.

In accordance with one embodiment of the invention, a fluid disruptor 19 also may be provided, which effects a detectable differential flow characteristic in the fluid path based on the direction of fluid flow. As shown in FIGS. 1 and 2, such fluid disruptor may include a mound 20, and a corresponding ledge 22 spaced from the mound so as to define a direction detection region 21 therebetween. When fluid flows in a first direction $D_1$, it will have a first flow characteristic within the direction detection region. The same fluid flow in a second direction $D_2$ will have a second, different flow characteristic within the direction detection region. In the embodiment depicted in FIGS. 1 and 2, this differential flow characteristic may be mass flow rate, which is related to temperature, and thus may be detected using the temperature sensors as will now be described.

Referring still to FIGS. 1 and 2, it will be noted that a reference temperature sensor 12 may be positioned within mound 20, and thus thermally isolated from fluid flow. Accordingly, temperature sensor 12 typically is not affected by changes in the flow of fluid within tube 18. Temperature sensors 14 and 16 are positioned on opposite sides of mound 20, typically in the fluid flow path. As indicated, temperature sensor 14 may be placed in a flow region 23, wherein the aforementioned flow characteristic (e.g., mass flow rate) is affected by flow volume, but not affected by flow direction. Temperature sensor 16 may be placed in a direction detection region 21 wherein the flow characteristic (e.g., mass flow rate) is affected by both flow volume and flow direction. Collectively, these temperature sensors provide information sufficient to determine flow direction by reviewing temperatures at various points along the flow path. This may be accomplished directly, by sensing actual temperatures, or indirectly, by detecting control signals in a modified anemometer circuit as will be described below.

Focusing now on the differential temperature experienced at each of the temperature sensors, it will be appreciated that exposed temperature sensors 14 and 16 may be influenced by increases and decreases in fluid flow. It also will be appreciated that temperature sensor 12 typically is thermally isolated from the fluid flow, and thus is not similarly influenced.

As shown in FIG. 1, upon fluid flow in the first direction $D_1$, flow remains substantially laminar over mound 20. Upon reaching direction detection region 21, however, the fluid collides with ledge 22, creating a high velocity turbulence in the vicinity of temperature sensor 16. The high velocity turbulence creates an efficient heat transfer, influencing the temperature detected by temperature sensor 16.

Referring to FIG. 2, it will be noted that fluid flow in the second direction $D_2$, flows along ledge 22, over direction detection region 21, and becomes substantially laminar over mound 20. Fluid moving over the ledge stagnates in the direction detection region, causing an eddy current, as indicated by arrow 21a. Although this fluid is somewhat turbulent, it has a lower velocity or mass flow rate than that depicted in the direction detection region of FIG. 1. Efficiency of heat transfer in the direction detection region in FIG. 2 is less than the efficiency of heat transfer in the direction detection region in FIG. 1, and the influence of fluid flow on the temperature detected by temperature sensor 16 is diminished.

Flow past temperature sensor 14 typically remains consistent regardless of flow direction. The influence on temperature sensor 14 offered by fluid flow thus typically does not change with flow direction, for a given flow volume. Conversely, as also indicated by arrows in FIGS. 1 and 2, flow past temperature sensor 16 differs with differing flow direction, leading to a differential influence on temperature sensor 16. Also, although not shown, it will be appreciated that temperature sensor 14 may be configured in a second direction detection region, similar to direction detection region 21, but with an opposite differential flow characteristic to that described above with respect to direction detection region 21.

Accordingly, by monitoring the temperature detected by temperature sensor 16 (for a given flow volume determined, for example, by temperature sensor 14) it is possible to determine flow direction in tube 18. In this context, temperature sensor 14 will be influenced by flow volume, but not flow direction, and thus may provide an effective volume reference. This allows distinction at temperature sensor 16 between a low volume flow in the first direction $D_1$ and a high volume flow in the second direction $D_2$. Correspondingly, where flow volume and ambient temperature are predictable, such a reference measurement may not be necessary.

Thus, if fluid is flowing from left to right, as in the tube shown in FIG. 1, exposed temperature sensor 14 typically will measure a lower temperature than protected temperature sensor 12 due to the effect of a fluid flow on temperature sensor 14. Furthermore, temperature sensor 16 typically will detect an even lower temperature than sensor 14 due to increased turbulence of the fluid flow adjacent temperature sensor 16. As indicated above, this increased turbulence in the area of temperature sensor 16 may be caused by fluid disrupter 19 when fluid flows in the first direction $D_1$, shown in FIG. 1. Therefore, in the depicted arrangement, when $T_{16} < T_{14} < T_{12}$, it can be determined that the fluid flow is from left to right (where $T_{12}$ is representative of the temperature detected by reference temperature sensor 12, $T_{14}$ is representative of the temperature detected by temperature sensor 14, and $T_{16}$ is representative of the temperature detected by temperature sensor 16).

If fluid is flowing from right to left, as in the tube shown in FIG. 2, exposed temperature sensor 14 again typically will measure a lower temperature than protected temperature sensor 12 due to the effect of a fluid flow on temperature sensor 14. However, as indicated above, the temperature detected by temperature sensor 16 may not be as substantially affected by fluid flow in the second direction $D_2$. Rather, temperature sensor 16 typically will detect a temperature greater than the temperature detected by temperature sensor 14 due to eddy fluid flow adjacent temperature sensor 16. As indicated above, this eddy fluid flow in the area of temperature sensor 16 may be caused by fluid disruptor 19 when fluid flows in the second direction, shown in FIG. 2. Accordingly, when $T_{14} < T_{16}$ (and $T_{14} < T_{12}$) in the arrangement shown, it can be determined that the fluid flow is from right to left.

Finally, if there is no measurable temperature differential between the sensors ($T_{12} \cong T_{14} \cong T_{16}$) then it can be determined that there is no measurable fluid flow. The sensitivity of the system can be adjusted by manipulating the sensitivity of each of the temperature sensors, by reconfiguring the fluid disruptor and/or by selecting a threshold temperature differential that must be detected before a particular flow direction is called.

In one embodiment, each temperature sensor could simply indicate the temperature it detects to the user, the user being charged with the task of interpreting the data. For example, the user could review the data to simply determine whether the exposed temperatures are disparate enough from the protected temperature to indicate a flow direction and, if so, could compare the temperatures measured by the temperature sensors exposed to the fluid flow to determine the direction of flow.

Alternatively, the temperature sensors could, with an appropriate comparator 232, form a part of control circuitry 30. In one particular embodiment, the control circuitry may take the form of a modified anemometer circuit constructed on a monolithic integrated circuit, which also may integrate control electronics of the fluid flow system. In essence, the modified anemometer circuit may include two sets of differential transistor pairs. Each transistor pair, in turn, may function as a hot-wire anemometer to sense flow adjacent a sense transistor of such transistor pair in view of a reference transistor. Both transistor pairs may employ common reference transistor. Each transistor pair, however, typically will employ a different sense transistor at a different position along the fluid flow path.

Alternatively, the reference transistor may be omitted where an absolute temperature reference is not required. Accordingly, one sense transistor may be referenced relative to another sense transistor.

In any event, the proposed sense arrangement may employ a plurality of monolithically-constructed sense elements configured for use as a reference wire and differential sense wires in a modified hot-wire anemometry circuit. This construction may provide greater resistance to breakage (e.g., due to shock) than do the thin wires used in known hot-wire anemometry systems. However, such monolithically-constructed sense elements typically will maintain rapid thermal response times, and thereby establish rapid system response time. Accordingly, the proposed sensor elements provide for reliable operation over rapidly varying loads and at acceptable system cost.

Figure 3:
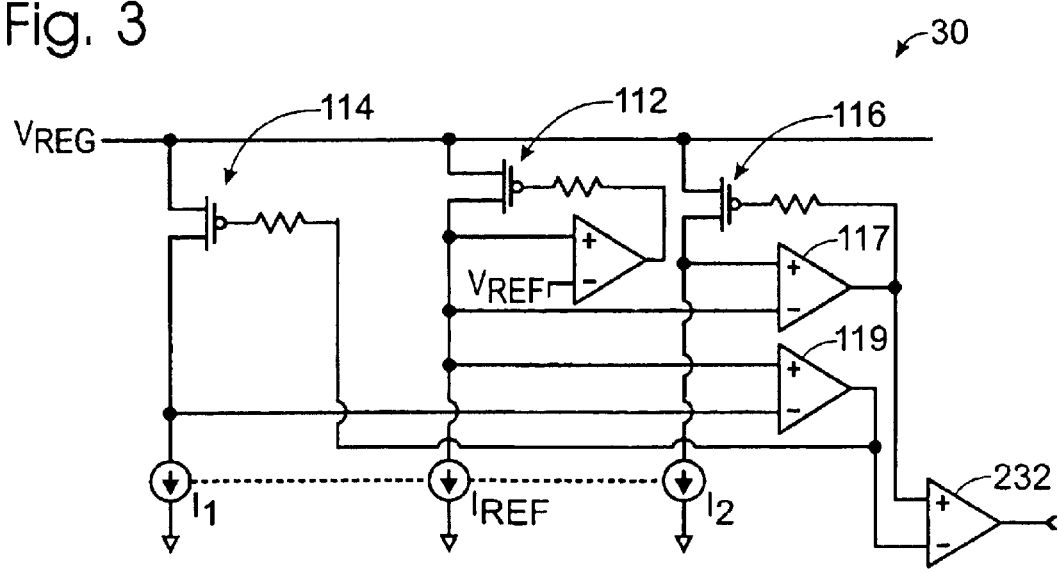
FIG. 3 is a schematic diagram of control circuitry suitable for use in processing sensed fluid flow characteristics.

FIG. 3 shows exemplary control circuitry 30 for use in the proposed flow direction detector, such control circuitry defining a sensor arrangement which employs a first transistor pair including a reference transistor 112 shielded from fluid flow, and a first sense transistor 116 disposed in the flow path (typically, in direction detection region 21). A second transistor pair also may be employed by the sensor arrangement, the second transistor pair including a reference transistor (which may or may not be the same as reference transistor 112) and a second sense transistor 114 disposed along the flow path (typically, in a flow region 23 outside of direction detection region 21). These transistor pairs may be arranged as indicated to effectively produce control signals indicative of temperatures adjacent each respective sense transistor (as related to a common reference temperature detected by reference transistor 112).

As shown, first sense transistor 116 may be operatively linked to reference transistor 112 via an amplifier 117 in a feedback loop, thereby providing for differing control signals (e.g. control voltages) under differing temperatures (which typically correspond to differing mass flow rates). The control signal effectively maintains a constant temperature at first sense transistor 116 relative to the temperature of reference transistor 112, and thus is itself an indicator of temperature adjacent the first sense transistor (e.g. in the direction detection region). This balance may be accommodated via provision of a regulated voltage ($V_{REG}$), and a reference current (as provided, for example, by current synch(s) ($I_{REF}, I_1$ and $I_2$)), as shown. A reference voltage ($V_{REF}$) also may be provided, typically as an input to an amplifier providing a control signal to reference transistor 112.

Second sense transistor 114 also may be operatively linked to reference transistor 112 via an amplifier 119 in a feedback loop, thereby providing for differing control signals (e.g. control voltages) under differing temperatures (which typically correspond to differing mass flow rates). The control signal effectively maintains a constant temperature at the second sense transistor relative to the temperature of the reference transistor, and thus is an indicator of temperature adjacent the second sense transistor (e.g. in the flow region, outside the direction detection region).

As stated above, a fluid disruptor may be provided such that temperature (and mass flow rate) change with fluid flow direction in the direction detection region, but do not change with fluid flow direction in the flow region. The fluid disrupter thus may serve to enhance thermal differential between the direction detection region and the flow region under differing directions of fluid flow. This, in turn, makes it possible to compare a direction-detection control signal ($V_1$) of the first sense transistor with a reference control signal ($V_2$) of the second sense transistor via a processor such as comparator 232 to determine direction of fluid flow. A first relationship between such control signals may be indicative of flow in a first direction. A second relationship between such control signals may be indicative of flow in a second direction.

In some instances, the comparator output may be fed to a logical AND device. A programmed ENABLE bit also may be fed to the logical AND device so as to provide for selectively enabling direction detection. Accordingly, where the present direction detection system is to be employed in a medical setting, such as in a metered dose inhaler, it is possible to provide the manufacturer, pharmacist or doctor with the ability to selectively enable/disable this function based on the medication, or on potential liability concerns.

It will be appreciated, of course, that the control circuitry herein described is exemplary only, and that various alternative hardware and software configurations may be employed. Furthermore, as indicated above, the control circuitry may be formed as a monolithic integrated circuit having monolithically constructed sense transistors which yield both excellent resistance to breakage and rapid response time. This may provide for reliable operation over rapidly varying loads while maintaining a relatively low system cost.

Figure 4:
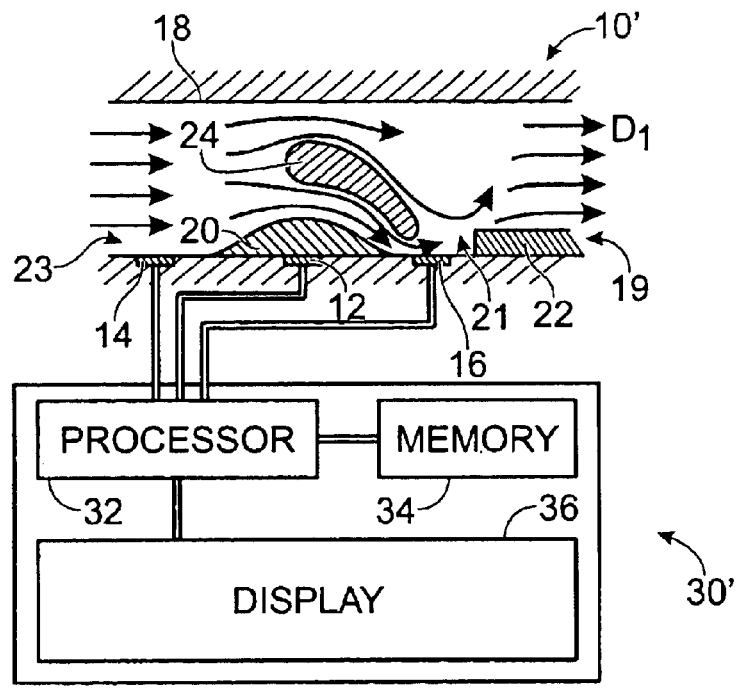
FIG. 4 is a somewhat schematic illustration of a flow direction detector according to another embodiment of the present invention, fluid being shown flowing in a first direction.
Figure 5:
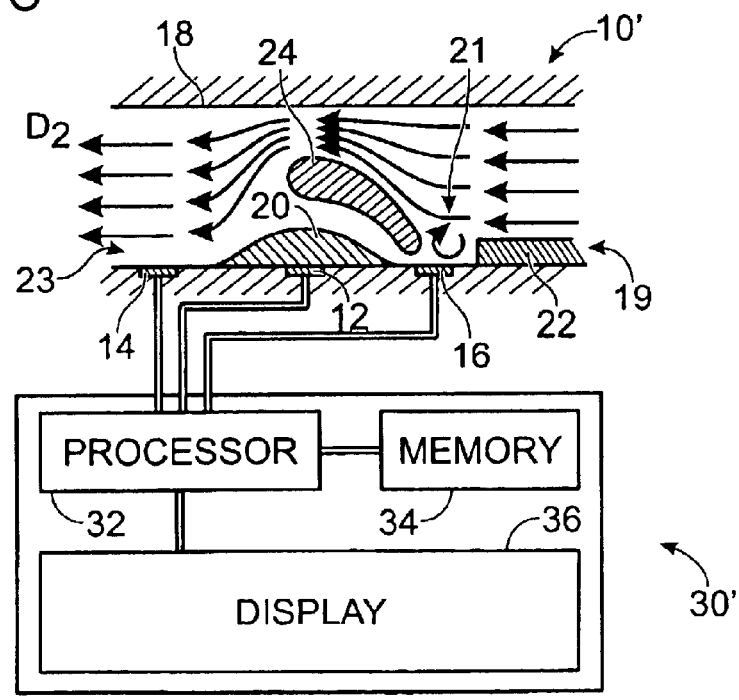
FIG. 5 is a somewhat schematic illustration of the flow direction detector of FIG. 4, but showing fluid flow in a second direction opposite the first direction.

Alternative configurations for the aforementioned fluid disrupter also may be used, including a configuration which employs further structure configured to promote or enhance detectable disruption in the fluid flow. In FIGS. 4 and 5, for example, an airfoil 24 is added to the flow direction detector of FIGS. 1 and 2. The resulting flow direction detector (indicated generally at 10') tends to promote the flow of fluid more directly toward temperature sensor 16 (in direction detection region 21) when fluid is flowing in the first direction ($D_1$), and/or tends to promote less flow of fluid toward temperature sensor 16 when fluid is flowing in the second direction ($D_2$). Accordingly, in FIG. 4, an enhanced laminar flow of fluid is shown in the vicinity of direction detection region 21 (as represented by converging arrows) when fluid flows left to right. In FIG. 5, a diminished overall flow of fluid is shown in the vicinity of direction detection region 21 (as represented by a swirled arrow indicating eddy currents) when fluid flows from right to left.

FIGS. 4 and 5 also show alternative control circuitry 30' which includes a processor 32 adapted to perform the comparisons described above so as to determine the direction of fluid flow. The control circuitry also may include memory 34 in which pre-selected, pre-programmed and/or user-selected operating parameters are stored. These operating parameters may be used to control the flow direction detector, and to interpret data produced thereby. The direction of fluid flow thus may be determined automatically, and communicated to the user via an indicator such as, for example, a display 36. Where the desired flow direction is known, the indicator may take the form of an alarm (aural or visual) which simply alerts the user when flow direction is other than that desired.

Fluid flow direction along a bi-directional fluid flow path thus may be determined via a method including disrupting fluid flow in the direction detection region differentially based on direction of fluid flow. Such differential disruption may take the form of differential mass flow rate, which, in turn, may have a corresponding differential effect on temperature within the direction detection region. The method may further include sensing mass flow rate (or temperature) within the direction detection region, sensing mass flow rate (or temperature) in the flow region, and comparing the sensed mass flow rates (or temperatures). As indicated above, a first detected relation between such mass flow rates (or temperatures) may be indicative of fluid flow in the first direction, and a second detected relation may be indicative of fluid flow in the second direction.

Furthermore, it will be appreciated that plural sets of sense elements may be configured in an array such that multi-dimensional flow may be resolved. For example, sensors may be arranged along each of X- and Y-axes in a fluid flow chamber such that fluid flow direction in the XY plane may be determined by the vector sum of detected flows along the X- and Y-axes. Flow direction in a 3-dimensional field similarly may be determined by the vector sum of detected flows along each of three orthogonal axes (e.g. X-, Y- and Z-axes) where sense element sets are arranged along each of such three orthogonal axes.

Figure 6:
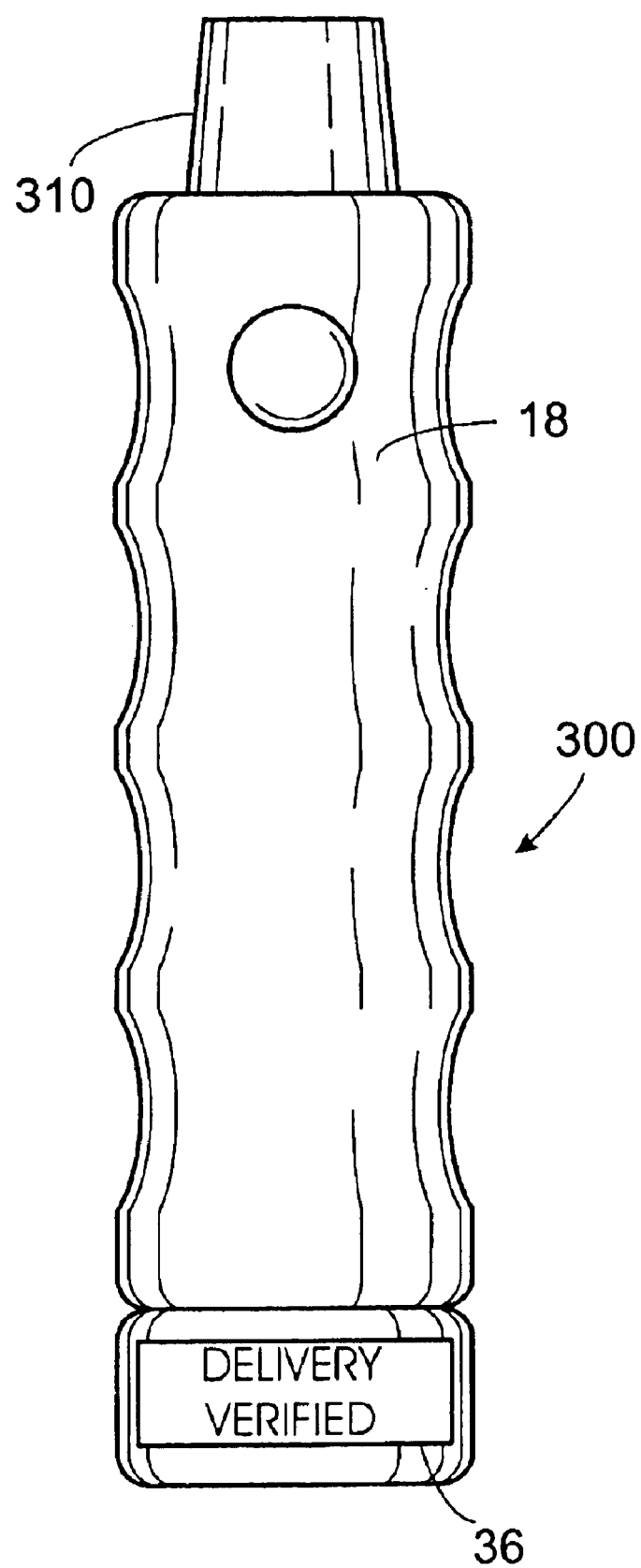
FIG. 6 is a plan view of a metered dose inhaler employing a flow direction detector according to one embodiment of the invention.

As will be appreciated, the flow direction detector is suitable for use in a wide variety of applications including metered dose inhalers, fuel injection systems and fuel processors. As a specific, non-limiting example, the present flow direction detector may be considered to be employed in a metered dose inhaler of the type shown in FIG. 6. Such an inhaler is indicated generally at 300 in FIG. 6. Inhaler 300 typically includes a pressurized supply of an inhalant mixed with an aerosol propellant or carrier. Accordingly, the user may place the inhaler's mouthpiece 310 in or over his mouth and/or nose and activate the inhaler. Activation of the inhaler will release a "puff" of the inhalant-propellant mixture from a medicament storage chamber into a medicament delivery tube (the interior of which is represented herein, for example, at 18 in FIGS. 4 and 5). As the medicament is released, the user aspirates the medicament in the medicament delivery tube by inhaling through his mouth and/or nose.

The aforementioned flow direction detector may be employed in the medicament delivery tube of the metered dose inhaler to allow verification of proper dosage by determining the direction of fluid flow with the medicament delivery tube. When a user inhales through the fluid delivery tube upon activation of the inhaler, a flow in a first direction $D_1$ may be initiated and maintained. The inhalant-propellant mixture thus typically will flow, in substantially laminar fashion, across temperature sensor 14, over barrier 20, across temperature sensor 16, over ledge 22, and finally out of the medicament delivery tube into the patient's mouth. In contrast, if the user exhales into the medicament delivery tube upon activation of the inhaler, fluid flow in a second direction $D_2$ may be initiated. In this second direction $D_2$, the inhalant-propellant mixture typically will flow across ledge 22, over mound 20, and over temperature sensor temperature sensor 16, over barrier 20, and then across temperature sensor 14. Due to the effect of the fluid disruptor when fluid flow is in the second direction $D_2$, the flow may effectively bypass temperature sensor 16 (in direction detection region 21). Mass flow rate within flow region 23, however, will remain independent of direction of fluid flow.

Accordingly, there typically will be a differential affect on the temperature detected by temperature sensor 16 based on the direction of fluid flow. Thus, as previously described with respect to FIGS. 1 and 2, when $T_{16}<T_{14}$, it typically can be determined that flow detected within the inhaler is indicative of the user inhaling, and thus of a proper dosing event. Conversely, when $T_{14}<T_{16}$, it typically can be determined that the flow detected within the inhaler is indicative of the user exhaling, and thus of an improper dosing event. In either event, $T_{14}<T_{12}$, indicating that there is a fluid flow within the inhaler. When there is no appreciable temperature differential between the temperature sensors, when $T_{12}<T_{14}$, or when the temperature differential does not exceed a predetermined threshold temperature, it can be determined that flow direction was not significant enough to determine whether the user has inhaled or exhaled.

As stated above, the metered dose inhaler may further include an indicator (such as display 36) configured to indicate to the user whether a correct dose has been administered. For example, the metered dose inhaler may employ a processor, such as processor 32 described above, to compare timing of a dosing directive of the metered dose inhaler with timing of a detected inhalation to verify proper delivery of inhalant to a user. Where the directive and delivery match in time, the indicator thus may be used to indicate proper delivery of inhalant to the user. This indicator may produce an audible or visible signal that can be perceived by the user after activation of the inhaler. For example, the inhaler may produce a sound, indicating that the user inhaled at an inappropriate time. Depending on the design of the metered dose inhaler, and the type of medication being administered, the user (or user's physician or pharmacist) can then make a decision regarding whether or not to administer another dose.

If the inhaler utilizes a flow direction detector that includes a processor, the processor may be in electronic communication with a variety of the components of the inhaler. For example, processor 32 may store within memory 34 information regarding the propriety of successive detected dosing events to record a history of metered dose inhaler use. Such information may include an indication of whether the user inhaled or exhaled at the time the dosing directive was effected, the time, the date, the amount of medicament left within the medicament storage chamber, and the like. This information may then be periodically communicated to the user, pharmacist and/or physician, as desired.

While this invention has been described in particular detail with respect to metered dose inhalers, the invention is not so limited, and, as described, is suitable for use in a variety of applications. Furthermore, the subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements. It is believed that the following claims particularly point out certain combinations and subcombinations that are directed to one of the disclosed inventions and are novel and non-obvious. Inventions embodied in other combinations and subcombinations of features, functions, elements and/or properties may be claimed through amendment of the present claims or presentation of new claims in this or a related application. Such amended or new claims, whether they are directed to a different invention or directed to the same invention, whether different, broader, narrower or equal in scope to the original claims, are also regarded as included within the subject matter of the inventions of the present disclosure.

What is claimed is:

1. A flow direction detector comprising:
   a flow disruptor positioned in a fluid flow path to promote laminar fluid flow across a direction detection region upon fluid flow in the first direction, and to promote non-laminar fluid flow over the direction detection region upon fluid flow in the second direction, thereby effecting a detectable differential flow characteristic to such flow path based on fluid flow direction; and
   a sensor arrangement configured to detect such detectable differential flow characteristic within the flow path.

2. The flow direction detector of claim 1, wherein the detectable differential flow characteristic is temperature.

3. The flow direction detector of claim 2, wherein the sensor arrangement includes a first temperature sensor.

4. The flow direction detector of claim 3, wherein the first temperature sensor is disposed along the flow path in the direction detection region, and the direction detection region is characterized by differing temperatures under differing directions of fluid flow.

5. The flow direction detector of claim 1, wherein the detectable differential flow characteristic is mass flow rate.

6. The flow direction detector of claim 5, wherein the flow disruptor includes a ledge configured to promote fluid flow across the direction detection region upon fluid flow in a first direction, and to promote fluid flow bypass of the direction detection region upon fluid flow in a second direction, the sensor arrangement being configured to detect corresponding differential mass flow rates in the direction detection region.

7. A flow direction detector comprising:
   a flow disruptor positioned in a fluid flow path to effect a detectable differential flow characteristic to such flow path based on fluid flow direction; and
   a sensor arrangement configured to detect such detectable differential flow characteristic within the flow path;
   wherein the flow disruptor includes a mound and a ledge configured to promote laminar fluid flow across an intermediate direction detection region upon fluid flow in the first direction, and to promote non-laminar fluid flow over the direction detection region upon fluid flow in the second direction, and wherein the sensor arrangement includes a first temperature sensor disposed within the direction detection region, the first temperature sensor being affected differentially by such laminar and non-laminar fluid flows.

8. The flow direction detector of claim 7, wherein the flow disruptor further includes a foil configured to further promote laminar fluid flow across the first temperature sensor upon fluid flow in the first direction, and to promote fluid flow bypass of the first temperature sensor upon fluid flow in the second direction, thereby enhancing differential sensed temperature based on fluid flow direction.

9. A flow direction detector comprising:
   a flow disruptor positioned in a fluid flow path to effect a detectable differential flow characteristic to such flow path based on fluid flow direction; and
   a sensor arrangement configured to detect such detectable differential flow characteristic within the flow path, wherein the sensor arrangement includes a first temperature sensor disposed in a direction detection region characterized by temperatures dependant on direction of fluid flow, and a second temperature sensor disposed in a flow region characterized by temperatures substantially independent of the direction of fluid flow.

10. The flow direction detector of claim 9, which further comprises a comparator configured to compare temperatures sensed by the first and second temperature sensors, a temperature sensed by the first temperature sensor which is lower than a temperature sensed by the second temperature sensor being indicative of fluid flow in the first direction.

11. The flow direction detector of claim 9, which further comprises a comparator configured to compare temperatures sensed by the first and second temperature sensors, a temperature sensed by the first temperature sensor which is higher than a temperature sensed by the second temperature sensor being indicative of fluid flow in the second direction.

12. A flow direction detector comprising:
   a flow disruptor positioned in a fluid flow path to effect a detectable differential flow characteristic to such flow path based on fluid flow direction;
   a sensor arrangement configured to detect such detectable differential flow characteristic within the flow path, wherein the sensor arrangement includes a first transistor pair including a reference transistor and a first sense transistor disposed along the flow path in a direction detection region characterized by differing mass flow rates under differing directions of fluid flow, the first sense transistor being operatively linked to the reference transistor in a feedback loop to provide for differing control voltages under such differing mass flow rates.

13. The flow direction detector of claim 12, wherein the sensor arrangement further includes a second transistor pair including the reference transistor and a second sense transistor disposed along the flow path in a flow region characterized by a mass flow rate substantially independent of the direction of fluid flow, the second sense transistor being operatively linked to the reference transistor in a feedback loop to provide a reference control voltage corresponding to such direction-independent mass flow rate, comparison of the control voltage to the reference control voltage being indicative of a direction of fluid flow.

14. The flow direction detector of claim 13, wherein the first and second transistor pairs share a reference transistor.

15. The flow direction detector of claim 14, wherein the fluid disruptor includes a mound and a ledge configured to promote turbulent laminar fluid flow across the direction detection region upon fluid flow in the first direction, and to promote less-turbulent eddy fluid flow in the direction detection region upon fluid flow in the second direction.

16. The flow direction detector of claim 15, wherein the fluid disruptor further includes a foil configured to further promote turbulent laminar fluid flow across the first temperature sensor upon fluid flow in the first direction, and to further promote less-turbulent eddy fluid flow across the first temperature sensor upon fluid flow in the second direction, thereby enhancing differential sensed temperature based on fluid flow direction.

* * * * *